United States Patent [19]

Nelson et al.

[11] Patent Number: 5,089,413

[45] Date of Patent: Feb. 18, 1992

[54] METHOD AND APPARATUS FOR CULTURING WITH MICROBIOLOGICAL DRY CULTURE MEDIUM

[75] Inventors: Robert L. Nelson, Bloomington; Paul E.L. Hansen, Lake Elmo, both of Minn.

[73] Assignee: Minnesota Mining and Manufacturing Company, St. Paul, Minn.

[21] Appl. No.: 354,627

[22] Filed: May 19, 1989

[51] Int. Cl.$^5$ .......................... C12N 1/00; C12M 1/16
[52] U.S. Cl. ........................ 435/254; 435/30; 435/34; 435/299; 435/313; 435/805; 435/818
[58] Field of Search .................. 435/30, 34, 299, 805, 435/243, 254, 313, 818

[56] References Cited

U.S. PATENT DOCUMENTS

| | | | |
|---|---|---|---|
| 2,954,327 | 9/1960 | Kanz | 435/299 |
| 3,184,395 | 5/1965 | Brewer | 195/80 |
| 3,814,670 | 6/1974 | Freake et al. | 195/127 |
| 3,843,452 | 10/1974 | Freake et al. | 195/103.5 |
| 3,843,456 | 10/1974 | Haden et al. | 435/299 |
| 4,250,256 | 2/1981 | Wielinger et al. | 435/32 |
| 4,271,270 | 6/1981 | Lukacsek | 435/299 |
| 4,476,226 | 10/1984 | Hansen et al. | 435/299 |
| 4,539,256 | 9/1985 | Shipman | 428/315.5 |
| 4,565,783 | 1/1986 | Hansen et al. | 435/299 |

Primary Examiner—David L. Lacey
Assistant Examiner—William H. Beisner
Attorney, Agent, or Firm—Gary L. Griswold; Walter N. Kirn; Douglas E. Reedich

[57] ABSTRACT

A device useful for growing aerobic microorganisms, particularly molds. The device employs a relatively small amount of water-reconstitutable medium that can be sealed in order to prevent desiccation and contamination of the medium yet still provide an adequate supply of air to the medium, by the use of a membrane underlying the medium, to support the growth of aerobic microorganisms.

18 Claims, 1 Drawing Sheet

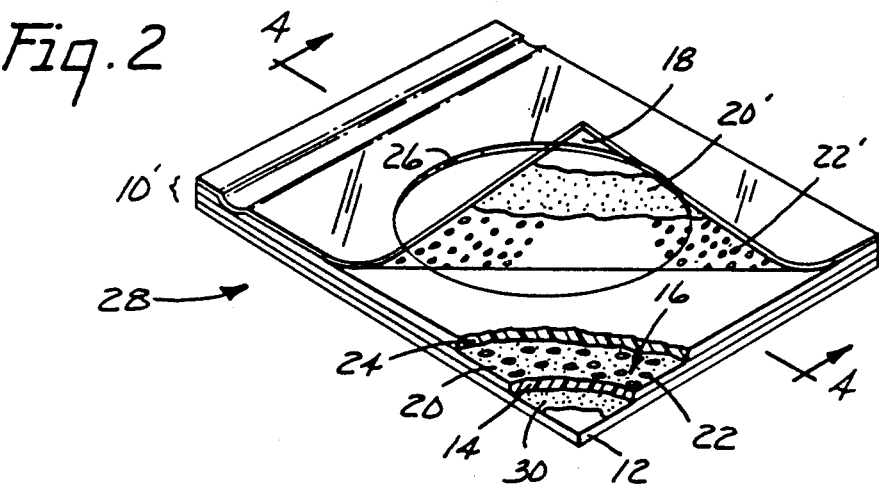
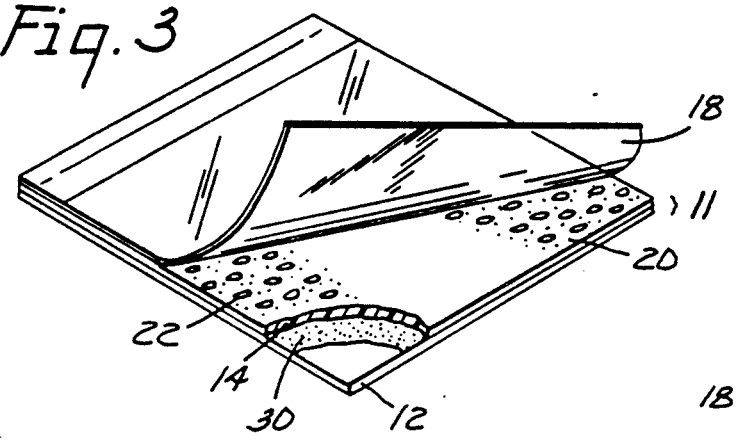
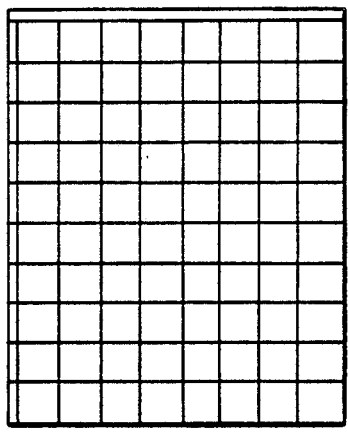
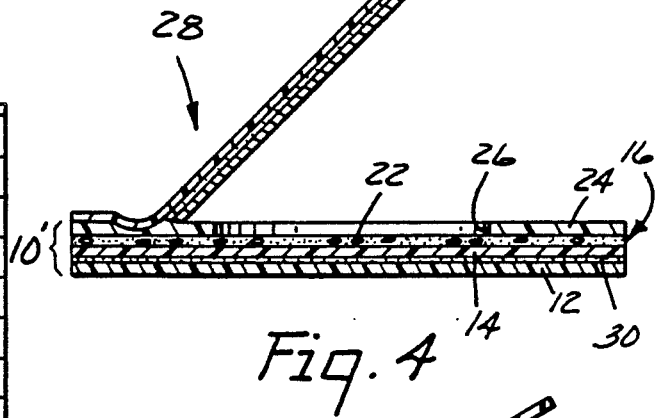

METHOD AND APPARATUS FOR CULTURING WITH MICROBIOLOGICAL DRY CULTURE MEDIUM

TECHNICAL FIELD

This invention pertains to devices that are useful for culturing microorganisms. Particularly, it pertains to such devices containing dry culture media capable of being reconstituted by water. In another aspect, this invention pertains to the use of such devices for the growth of microorganisms, such as many molds, that require oxygen.

BACKGROUND ART

A medium for culturing microorganisms can be prepared by dispersing gelling agent in an aqueous solution containing nutrients and other ingredients necessary for the growth of microorganisms. Unfortunately, the use of conventional gelling agents is often inconvenient for the end-user. For example, when carrying out standard "plate count" or "pour plate" methods to determine the number of microorganisms in a liquid sample such as water or milk, the use of agar as a gelling agent is particularly inconvenient and time-consuming. The agar-containing medium, which has generally been prepared in bulk and sterilized ahead of time, must be melted, for example, in boiling water or by exposure to steam. The hot medium must then be carefully cooled to approximately 45° C. A series of dilutions of a test sample is then prepared and an aliquot of each dilution is placed in a petri dish. The partially cooled, but still liquefied, medium is then poured into each dish, mixed with the aliquot of test sample, and allowed to solidify. After incubation, the colonies growing in each dish are counted by visual inspection. In this manner the number of colony-forming units ("CFU", i.e., microorganisms capable of forming colonies) originally present in the test sample can be determined.

Simpler methods exist, wherein the need for the end-user to manipulate the agar-containing medium can be eliminated, and significantly less medium need be used. For example, U.S. Pat. No. 4,565,783 discloses a device that provides the user the opportunity to perform standard plate counts in bacterial assays without manipulating an agar-containing medium. This device contains a powdered dry culture medium adhered to a waterproof substrate. Upon inoculation of the device with an aqueous sample suspected of containing microorganisms, the medium is reconstituted to form a homogeneous gel-like medium suitable for quantitative culturing of the microorganisms present in the sample. One such device (Petrifilm TM brand growth medium, available from 3M Company, St. Paul, Minn.) is particularly useful for the assay of bacteria.

In various industries, such as the dairy, fruit juice, wine, and beer industries, there exists a need to assay not only bacteria but also molds. The art does not typically distinguish mold assays from bacterial assays when devices for the assay of microorganisms are discussed, but it is known to those skilled in the art that mold assays are often more difficult than bacterial assays. One reason for this difficulty is that some molds require more oxygen for growth than do most bacteria, and thus some devices (e.g., devices that are covered or otherwise sealed off from outside air, as are many devices useful for bacterial assays) are unsuitable for use with molds. Also, some molds tend to grow homogeneously throughout a culture medium rather than in discrete, countable colonies.

Devices and methods for the growth of microorganisms known in the art generally involve incubation either in an environment open to air (e.g., in a petri dish), in order to allow an adequate supply of air to the medium, or in a sealed environment to prevent desiccation of the medium. Either approach is generally satisfactory when the devices use relatively large amounts of water and medium. Where relatively small amounts of water and medium are used, however, such as with Petrifilm TM brand growth medium, the user is faced with the following problem: if the device is allowed an adequate supply of air, the water can evaporate, thereby drying out the medium during incubation; on the other hand, if the device is sealed off, the air supply might be insufficient to sustain growth of microorganisms that require more oxygen.

One approach to the problem is seen in the Millipore Corp. (Bedford, Mass.) "Yeast and Mold Swab Sampler" used for the analysis of aqueous solutions. This device consists of a plastic tab supporting a microporous filter bonded to an absorbent pad that contains dehydrated nutrient medium. An aqueous sample passes through the filter into the pad, thereby isolating any microorganisms on the filter while hydrating the absorbent pad and the nutrient medium. The device is then placed in a container, with the plastic tab serving to seal the container. There is sufficient air in the container to support the growth of yeasts and molds. Nutrients are intended to pass from the medium into the filter, thus allowing the growth of microorganisms in the filter.

Certain other devices and methods that involve a water- or nutrient-permeable barrier (e.g., a membrane) to microorganisms are known to be useful for the growth of microorganisms. For example, U.S. Pat. Nos. 3,814,670, 3,843,452, and 4,250,256, disclose such devices. In no such device, however, does it appear that the barrier itself is used to provide an adequate supply of air to the growing microorganisms.

SUMMARY OF THE INVENTION

This invention provides a device useful for growing microorganisms, particularly aerobic microorganisms such as molds. While employing a relatively small amount of medium, the device can be sealed in order to prevent desiccation and contamination of the medium and still provide an adequate supply of air to the medium in order to support the growth of aerobic microorganisms in the medium.

The device of the invention comprises a body member having a growth region for growing microorganisms, which body member comprises:

(1) a waterproof substrate having a top surface and a bottom surface;

(2) an air-permeable membrane substantially exposed at its edge(s) to air, the membrane having a top surface and a bottom surface, the bottom surface being fixed to and covering at least the growth region of the top surface of the substrate; and (3) cold-water-reconstitutable dry medium fixed to and covering at least the growth region of the top surface of the membrane and containing at least one ingredient selected from the group consisting of one or more gelling agents and one or more nutrients for growing microorganisms. Preferably, the device further comprises cover means covering at least the growth region of the dry medium and capable of preventing contamination and dessication of the growth region.

The presence of the air-permeable membrane in the device of the invention solves the above-mentioned problem by providing an adequate air supply to the overlying medium. The device of the invention can be easily made by hand or with simple laboratory equipment. A preferred device of the invention can be used in much the same manner as the device disclosed in U.S. Pat. No. 4,565,783, i.e., the medium in the growth region of the device can be rehydrated with an aqueous sample suspected of containing microorganisms in order to reconstitute the dry medium. The device can then be covered with cover means, incubated, and analyzed visually to determine the number of colonies grown.

The device allows enumeration of colonies growing in the medium, such as mold colonies, in the same manner as colonies growing on a conventional agar medium in a petri dish. Moreover, the number of colonies obtained in an assay using a device of the invention correlates well with the number of colonies obtained in standard agar assays. The device has the added feature of using far less medium than is used in standard agar assays, and is much more compact and lightweight. Furthermore, a preferred device is disposable, allowing for safer and more rapid clean-up after use.

BRIEF DESCRIPTION OF THE DRAWING

The invention is further illustrated by reference to the accompanying Drawing wherein:

FIG. 1 is a cross-sectional view of a device of the invention, wherein certain salient features are shown.

FIG. 2 is a top perspective view, partially in section, of a preferred device of the invention;

FIG. 3 is a top perspective view of an alternative embodiment of the invention;

FIG. 4 is a cross sectional view of device of FIG. 2 taken along line 4—4;

FIG. 5 is a top view of the device of FIG. 2 showing a grid pattern printed on the microporous membrane.

DETAILED DESCRIPTION OF THE INVENTION

As used in the instant specification and claims,

"air-permeable" designates a membrane that, when substantially exposed at its edge(s) to air, is sufficiently permeable to air in the horizontal direction (i.e., parallel to its surfaces) to provide an adequate supply of air to the overlying medium in order to support the growth of aerobic microorganisms in the medium;

"cold-water-reconstitutable" designates material that is suspendible in water, e.g., forms a dispersion, solution or gel in room temperature water;

"cold-water-soluble" designates a cold-water reconstitutable material that forms a solution or gel in room temperature water;

"growth region" designates the region of each component of a device in which microorganisms are intended to be grown;

"powder" designates a particulate material, e.g., of nutrient and/or gelling agent, wherein the particles have an average diameter suitable for use in a device of the invention, e.g., an average diameter of less than about 400 $\mu m$;

"reconstituted medium" designates a cold-water-reconstitutable medium that has been rehydrated with water or an aqueous test sample;

"substantially impermeable to microorganisms and water vapor" designates cover means that (i) prevent undesired contamination of the underlying medium during shipping, storage, and use of the device and (ii) avoid desiccation of the medium, i.e., that maintain a level of hydration in a reconstituted medium suitable to support the growth of microorganisms during the incubation period; and "substantially water-free" designates a water content no greater than about the water content of the ambient environment.

With reference to FIG. 1, a preferred device of the invention is shown as body member 10 with three salient features: waterproof substrate 12, air-permeable membrane 14, and dry medium 16. Although these can be arranged in any suitable relationship, FIG. 1 illustrates a preferred arrangement of these components, wherein air permeable membrane 14 is fixed to and covers at least the growth region of the top surface of substrate 12. Dry medium 16 is fixed to and covers at least the growth region of the top surface of membrane 14. Cover means 18 for covering the dry medium during shipping, storage, and incubation, is also shown in FIG. 1 as being attached in a hinge-like fashion along one edge of body member 10. Cover means are optional but preferred in devices of the present invention. Suitable substrates, dry media and cover means include those described in U.S. Pat. No. 4,565,783, the disclosure of which is incorporated herein by reference.

Substrate 12 is preferably a relatively stiff waterproof film made of a material, such as polyester, polypropylene, or polystyrene, that will not absorb or otherwise be adversely affected by water. Polyester films about 100 $\mu m$ to about 180 $\mu m$ thick, polypropylene films about 100 $\mu m$ to about 200 $\mu m$ thick and polystyrene films about 300 $\mu m$ to about 380 $\mu m$ thick have been found to work well. Other suitable substrates include paper having a polyethylene or other water-proof coating. An example of a suitable polyethylene-coated paper substrate is "Schoeller Type MIL" photoprint paper (available from Schoeller Pulaski, New York). Substrate 12 can be transparent if one wishes to view colonies through the substrate.

Air-permeable membrane 14 allows an adequate supply of air to medium 16 when cover means 18 is in place over the medium. In so doing, membrane 14 is useful for supporting growth of aerobic microorganisms in the medium. It is also useful in instances where the microorganisms require air for reasons in addition to or other than for growth, for example, to oxidize a dye that renders the microorganism colonies more easily visible, as discussed more fully below.

By virtue of the air permeability of the membrane and the membrane being substantially exposed at its edge(s) to air, air is able to pass into the edge(s) of the membrane, horizontally through the membrane, and into the medium. Horizontal passage of air for a particular membrane is most conveniently estimated by evaluating the vertical air permeability of the membrane (i.e., permeability in a direction normal to the top and bottom surfaces of the membrane). Vertical air permeability can be determined by any suitable means. For purposes of the instant specification and claims, air permeability is determined by ASTM-D-726-58 Method A using a Gurley densometer to measure the time in seconds needed to pass 50 ml of air through the membrane (i.e., generally the membrane itself, absent any adhesive coating, medium, substrate, etc.). This permeability is referred to herein as Gurley porosity. It is preferred that the membrane have a Gurley porosity value of less than about 100 seconds, more preferably less than about 50 seconds, and most preferably less than about 25 seconds.

Those skilled in the art will recognize that the range of suitable membrane thickness will depend in part upon the air and water permeability of the membrane. In general, a uniform thickness between about 10 μm and about 500 μm is suitable, a uniform thickness between about 20 μm and about 100 μm is preferred, and a uniform thickness between about 40 μm and about 80 μm is particularly preferred.

Suitable membranes include, but are not limited to, microporous films and microporous non-woven webs of synthetic or natural materials. Such membranes are readily available, and methods of preparing them are well known to those skilled in the art. Preferred membranes for use in a device of the invention include microporous membranes prepared, e.g., as described in Example 23 of U.S. Pat. No. 4,539,256, the disclosure of this patent being incorporated herein by reference. These preferred membranes can be made of any polymer suitable for use in the method of preparation described in the '256 patent.

Particularly preferred are membranes made of polypropylene, polyethylene, polyethylene terephthalate, polybutylene terephthalate, nylon, polyvinylidine fluoride, or copolymers or blends thereof. Examples of preferred membranes include Exxaire TM breathable polyolefin film (50 μm thick, Gurley porosity about 50 seconds, available as product number 10 B04 from Exxon Chemical Co., Polymers Group); Exxaire TM breathable polyolefin film (50 μm thick, Gurley porosity about 100 seconds, available as product number 7 B03 from Exxon Chemical Co., Polymers Group); microporous polyethylene film (20 μm thick, Gurley porosity about 25 seconds); and 3M Micropore TM tape, which has a non-woven rayon web as backing, and that as a tape, i.e., with adhesive, is 125 μm thick and has a Gurley porosity about 0.1 seconds (product number 1530, 3M Company, St. Paul, Minn.).

The membrane preferably has a visible square grid pattern printed upon it, as shown in FIG. 5, to facilitate the counting of microorganism colonies.

As regards dry medium 16, any suitable form of dry medium that is cold-water-reconstitutable can be used in the device of the invention. Such media are well known. Generally in the device of the invention the cold-water-reconstitutable dry medium contains at least one ingredient selected from the group consisting of one or more gelling agents and one or more nutrients for growing microorganisms.

Suitable gelling agents for use in dry medium 16 include cold-water-soluble natural and synthetic gelling agents. Natural gelling agents such as algin, carboxymethyl cellulose, hydroxyethyl cellulose, guar gum, locust bean gum, xanthan gum, and synthetic gelling agents such as polyacrylamide, are generally suitable. Selection of gelling agent is of particular importance when a device of the invention is intended for use in mold assays. Some gelling agents, such as guar gum, are not suitable for use in certain mold assays because of the ability of molds to metabolize such gelling agents. Appropriate gelling agents can be selected according to the teaching of this invention consistent with the use intended for the device. Preferred gelling agents include locust bean gum and xanthan gum, these gelling agents being useful individually, or preferably, in combination with one another.

As indicated above, the dry medium can contain gelling agent only, and no nutrient. Before the addition of an aqueous sample suspected of containing microorganisms, the user can add nutrients tailored to the type of microorganisms to be grown. For example, dry powdered nutrients can be suspended in a rapidly-evaporating liquid such as ethanol or a volatile chlorofluorocarbon. In other instances, dry powdered nutrients can be suspended, e.g., dispersed or dissolved, in aqueous solutions. In either case, when an aliquot of the nutrient suspension or solution is added to the surface of the medium, the liquid can be allowed to evaporate, leaving ample nutrients along with the gelling agent.

Conversely, the dry medium can contain nutrients only, and no gelling agent. Gelling agent is generally only required if one desires to visualize, count, and/or isolate discrete colonies. In many microbiological tests, such as tests for bacteria identification or antibiotic susceptibility, broth media are used, and there is no need for a viscous gel. In devices for carrying out such tests, the gelling agent can be omitted.

The particular nutrients suitable for use in the dry medium will depend on the microorganism to be grown in the device, and will be easily selected by those skilled in the art. Generally, such nutrients are cold-watersoluble.

The dry medium can include any number of other components, such as dyes, crosslinking agents, or reagents such as antibiotics. For example, for some uses it is desirable to incorporate a dye in the dry medium, or, as described in detail below, in the adhesive of an adhered powder medium. Suitable dyes include those that are metabolized by or otherwise react with the growing microorganisms, and in so doing cause the colonies to be colored or fluorescent for easier visualization. Such dyes include triphenyl tetrazolium chloride, p-tolyl tetrazolium red, tetrazolium violet, veratryl tetrazolium blue and related dyes, and 5-bromo-4-chloroindolyl phosphate disodium salt. Other suitable dyes include those sensitive to pH changes during the growth of microorganisms, such as neutral red.

For some uses it is desirable to form a dry medium that, when reconstituted, is stiff enough to allow inoculation by streaking. To form streakable medium, an effective amount of a suitable cross-linking agent can be incorporated into a dry medium that includes a gelling agent. Suitable cross-linking agents do not substantially affect the growth of the intended microorganisms. Suitable types and amounts of cross-linking agents are easily selected by those skilled in the art. For example, with guar gum, cross-linking agents such as potassium tetraborate, aluminum salts, or calcium salts are suitable, and can be added in effective amounts, e.g., less than about 1.0 percent by weight of dry medium.

The dry medium can optionally include reagents necessary for carrying out certain microbiological tests. For example, antibiotics can be included for carrying out antibiotic susceptibility tests. For microorganism identification, reagents that undergo a color change in the presence of a particular type of microorganism can be included. To grow a yeast or mold sample without interference from bacteria, bacteriostatic or bactericidal agents such as chloramphenicol, chlortetracycline, tartaric acid, or a suitable penicillin can be included in the dry medium.

A device of the present invention preferably includes cover means, such as cover sheet 18 as illustrated in FIG. 1, adapted to cover at least the growth region of the medium. Cover means are preferably transparent in order to facilitate the counting of colonies, and are substantially impermeable to microorganisms and water vapor. Generally, cover means can be made of materials such as those used to make substrate 12. Since air is supplied to the medium via air-permeable membrane 14, cover means need not be selected to allow air transport to the medium. The presently preferred material for cover means is polypropylene, e.g., in the form of a 40 μm thick biaxially-oriented polypropylene film.

Cover means can be free of any coating, or can be coated, e.g., on the surface facing the dry medium with a layer of pressure-sensitive adhesive, in order to facilitate sealing of the cover means over the medium. Furthermore, cover means such as cover sheet 18 illustrated in FIG. 2, can optionally be coated on the surface facing the dry medium with layers of adhesive 20' and powder 22', that are the same as or different from adhesive 20 and powder 22 of an adhered powder medium (described in detail below). Coatings on cover sheet 18 can cover the entire surface facing the dry medium, but preferably cover at least the part of the surface that is intended to cover the growth region of the medium. Such coated cover sheets are particularly preferred when it is desired to provide a device with more gelling agent than can be incorporated in the dry medium alone.

A device of the invention can also include spacer means between the medium and cover means, in order to create a well that serves to both define the growth region of the medium and confine an aqueous sample to the growth region of the medium. Spacer means are illustrated in FIG. 2 as spacer 24 defining a circular hole 26. The walls of hole 26 provide a well of predetermined size and shape over the growth region of the medium. Spacer 24 should be thick enough to form a well of the desired volume, e.g., 1, 2, or 3 ml, depending on the size of the growth region and the size of sample to be placed on the medium. Preferably spacer 24 is made of closed cell polyethylene foam but any material that is hydrophobic (non-wetting), inert to microorganisms, and sterilizable can be used.

A device of the invention can be prepared using a variety of techniques. Generally, a device can be made by hand or with common laboratory equipment as described in detail below.

FIGS. 2 and 4 illustrate a device in accordance with the present invention. Device 28 includes a body member 10' having a water-proof substrate 12 with a top surface and a bottom surface. The bottom surface of membrane 14 is fixed to (e.g., fixed with an adhesive or otherwise attached to) at least the growth region of the top surface of substrate 12. Preferably, the top surface of substrate 12 is coated with adhesive layer 30, which is used to fix membrane 14. Adhesive layer 30 is preferably pressure-sensitive, insoluble in water, and substantially non-inhibitory to the growth of the intended microorganisms. Preferred adhesives include those discussed below in connection with adhesive layers 20 and 20'. Often, suitable substrates are available already coated with a suitable adhesive. If one desires, however, a suitable substrate can be selected and coated (e.g., using a knife coater) with a suitable adhesive.

The method of fixing membrane 14 to substrate 12 will depend on the nature of adhesive layer 30. If adhesive layer 30 is pressure sensitive for instance, membrane 14 can be placed on adhesive layer 30, pressed down, and thereby adhered in place.

Dry medium 16 is fixed in any suitable manner to and covers at least the growth region of membrane 14. Adhered powder media and coated media, discussed more fully below, are the preferred forms of medium 16, and the method of fixing medium 16 to membrane 14 will depend on the form of medium 16.

An adhered powder medium, illustrated in FIGS. 2 and 3, is prepared and fixed by first forming a layer 20 of adhesive on at least the growth region of the top surface of membrane 14. The adhesive is preferably pressure-sensitive, insoluble in water, and substantially non-inhibitory to the growth of the intended microorganisms. Preferably, adhesive layer 20 is also sufficiently transparent when wet to enable viewing of microbial colonies.

The presently preferred pressure-sensitive adhesive is a copolymer of 2-methylbutylacrylate/acrylic acid in a mole ratio of 90/10 (3M Company, Specialty Chemicals Division, St. Paul, Minn.). Other preferred pressure-sensitive adhesives that can be used include isooctylacrylate/acrylic acid in a mole ratio of 95/5 or 94/6 (3M Company, Specialty Chemicals Division, St. Paul, Minn.) and silicone rubber. Adhesives that turn milky upon exposure to water are less preferred, but can be used in conjunction with a non-transparent substrate or in situations where colony visualization is not required. When incorporating a dye as described above in order to facilitate visualization of colonies, it is generally preferred to incorporate the dye in the adhesive rather than in the powder.

The adhesive is coated (e.g., using a knife coater) onto the top surface of membrane 14 to form layer 20 at a thickness that is preferably less than the average diameter of the particles of powder 22. Generally, enough adhesive is coated to adhere the particles to membrane 14 but not so much that the particles become completely embedded in the adhesive. Generally an adhesive layer about 5 μm to about 12 μm thick is suitable.

In order to form an adhered powder medium, a layer of cold-water-soluble powder 22 is then adhered substantially uniformly to at least the growth region of adhesive layer 20.

Powder 22 can contain the components discussed above in connection with dry media. Preferably, when gelling agent is included in powder 22, it is included in an amount such that a predetermined quantity of water or an aqueous sample, e.g., 1 to 3 ml, placed on the medium will form a reconstituted medium having a suitable viscosity, e.g., about 1500 cps or more when measured at 60 rpm with a Brookfield Model LVF viscometer at 25° C. Media of this viscosity allow convenient handling and stacking of the devices during incubation and provide for distinct colony formation in the medium. For instance, 0.025 g to 0.050 g of powdered guar gum spread substantially uniformly over a surface area of 20.3 cm$^2$ will provide a sufficiently viscous medium when reconstituted with 1 to 3 ml of an aqueous sample. The size of the powder particles can be used to control the coating weight per unit area. For example, under conditions where a 100 mesh guar gum coats to a weight of about 0.05 g/20.3 cm$^2$, a 400 mesh guar gum coats to a weight of about 0.025 g/20.3 cm$^2$.

The preferred ratio of gelling agent to nutrient in an adhered powder medium is determined by the particular microorganism to be grown on the device. For general purposes, however, a ratio from about 4 to 1 to about 5 to 1 (total gelling agent to total nutrient, based on weight) is preferred.

The powder 22 in an adhered powder medium can be applied to the adhesive layer 20 by any means suitable for the application of a substantially uniform layer. Preferred methods include the use of a shaker-type device, or the use of a powder coater.

The other preferred form of dry medium, i.e., a coated medium, is prepared as a substantially water-free coating, coated directly on at least the growth region of the top surface of the membrane. Coated media are generally self-adherent to the membrane and do not require a layer of adhesive between the membrane and the medium.

A coated medium can be prepared by making a solution containing gelling agent and/or nutrient, coating the solution (e.g., using a knife coater) onto the membrane, and allowing the coating of solution to dry. In addition to the suitable gelling agents described above, agar is a suitable cold-water-reconstitutable gelling agent for use in a coated medium. Gelling agent can also serve to thicken the medium solution in order to facilitate its coating onto the membrane. For practical purposes, the amount of gelling agent is preferably less than that which will cause the solution to thicken to the point where it is not practical to coat the medium onto the membrane.

A device of the present invention can also include spacer means and preferably includes cover means. Optional spacer means can be fixed between medium 16 and a cover sheet 18 by any suitable means. For example, it can be adhered to the membrane 14 via adhesive layer 20. The spacer can be fixed by pressing it against pressure-sensitive adhesive layer 20.

Cover sheet 18 is preferably adhered in a hinge-like fashion along one edge of spacer 24, and is optionally coated with adhesive layer 20' and powder 22'. Alternatively, cover sheet 18 can be adhered directly to the substrate 12 as illustrated in FIG. 3.

A device of the invention is particularly useful for growing aerobic microorganisms, and especially aerobic molds. Generally, use of a device of the invention involves the conventional steps of inoculation, incubation and isolation and/or analysis.

The use of a preferred device of the invention is discussed below with specific reference to the device of FIGS. 2 and 4, in which the medium is of the powder-/adhesive type.

To use the device of FIGS. 2 and 4, transparent cover sheet 18 is pulled back by the user and a predetermined quantity of water or an aqueous test sample is placed, e.g., pipetted, on the dry medium within the growth region of the medium, which in the illustrated embodiment is shown as hole 26 defined by spacer 24. The dry medium thereby becomes reconstituted. Cover sheet 18 is then replaced over the reconstituted medium, and the sample is spread evenly over the growth region, for example by placing a weighted plate on top of the covered device. The device is then incubated at a suitable temperature and for a suitable time in order to allow the growth of microbial colonies. Colonies growing in the medium can be counted through transparent cover sheet 18. If desired, colonies can be removed from the medium for further identification and/or analysis.

The embodiment of device 11 illustrated in FIG. 3 is identical to that of FIG. 2 except that spacer 24 is not present in FIG. 3. To use such an embodiment, a template (e.g., a weighted circular ring defining the growth region) can be applied temporarily on top of cover sheet 18, after closing, to confine reconstitution of the medium to the growth region of the medium.

The following EXAMPLES are intended to illustrate the invention. They are not intended to limit the invention.

EXAMPLES

EXAMPLE 1

Preparation of Devices

A strip of microporous polyethylene membrane, 20.3 cm wide by 30.5 cm long and about 50 $\mu$m thick (porous polyethylene, available as Advent ™ film product number 70-0000-4011-6, 3M Company, St. Paul, Minn.) was laminated by hand to the adhesive surface of a strip of polyethylene-backed pressure sensitive tape, 19.7 cm wide by 30.5 cm long, and 100 $\mu$m thick ("crepe" tape, product number 43-9100-5976-5, 3M Company, St. Paul, Minn.).

An adhesive solution to fix the medium to the membrane was made up as follows:

The dye 5-bromo-4-chloro-3-indolylphosphate disodium salt (0.2 g), chloramphenicol (0.03 g), and chlortetracycline (0.03 g) were dissolved in methanol (40 ml). The resulting solution was added to 100 ml of 48% (by weight) solution of a copolymer of 2-methylbutylacrylate and acrylic acid in a mole ratio of 90/10 (3M Company, Specialty Chemicals Division, St. Paul, Minn.) in 65/35 (v/v) heptane and acetone. The solution was stirred until it appeared homogeneous.

The adhesive solution was then coated on the membrane surface of the laminate, using a lab knife coater, at a final dry coating weight of 24.5 mg/100 $\mu$m$^2$. The coated laminate was allowed to dry in air.

A mixture of powdered nutrients and powdered gelling agent in a 1:4 ratio (by weight) was prepared. The nutrient was a powdered nutrient available from Acumedia Corp., Baltimore, Md., 0.455 kg of which contains 200 g brain heart infusion, 200 g glucose, 54 g neopeptone, 1.0 g calcium chloride, and 0.2 g water. The gelling agent was a mixture (1:1 by weight) of xanthan gum (Kelco Co., San Diego, Calif.) and locust bean gum (Hi-Tech Polymers, Inc., Louisville, Ky.). The nutrient and gelling agent powder mixture was sterilized with ethylene oxide, thoroughly aerated to remove all traces of residual sterilant, and was screened to a size such that 90% passed through a 100-mesh screen. The powder mixture was fixed on the adhesive coating with a powder coater at a weight of about 40 mg/100 cm$^2$. This powder-coated article served as the body member of the device.

A transparent pressure sensitive tape (Transparent Box Sealing Tape, 3M Company, St. Paul, Minn.), 40 $\mu$m thick, 35.5 cm long and 20.3 cm wide was used as cover means for the device. The tape was coated on its adhesive surface with the same powder, and in the same manner and at the same coating weight, as the body member described above.

The device was assembled by placing a strip of double coated pressure-sensitive tape (No. 1522 Double Coated Tape, 3M Company, St. Paul, Minn.) along the center of the body member's powdered surface, placing the cover means carefully over this, powder side down, and pressing the two sheets together by hand along the strip of double coated tape. The article thus obtained was cut with a scissors down the center of the strip of double coated tape. Each of the resulting two pieces was cut with a scissors at 7.6 cm intervals in order to obtain 8 devices, each of a size 7.6 cm by 10.2 cm.

The resultant devices were sterilized with gamma radiation, (3 megarads) before use, and are referred to herein as plates.

EXAMPLE 2

Evaluation of the Effect of Membrane Porosity On Mold Growth

Plates were prepared according to the process of EXAMPLE 1 above using different membrane materials. The membranes are listed in TABLE A below. The tape of Plate No. 1 was used with its adhesive side toward the substrate, and the Gurley porosity is that of the tape itself (i.e., membrane backing with adhesive).

TABLE A

| Plate No. | Membrane | Gurley Porosity (sec/50 cc) |
|---|---|---|
| 1 | Micropore TM tape (3M Company, St. Paul, MN) a non-woven rayon 125 μm thick | 0.1 |
| 2 | Microporous polyethylene film, made according to Example 23 U.S. Pat. No. 4,539,256, 50 μm thick | 16–25 |
| 3 | Microporous Polyethylene film (Exxair TM , Exxon Chemical Co.) 50 μm thick | 100 |
| 4 | Polyurethane film 50 μm thick | 1000 |
| 5 | No membrane | — |

The effect of membrane porosity was evaluated by attempting to grow several molds on each of the plates described above. Cultures of various molds were made into aqueous suspensions using standard methods.

Plates 1–5, described above, were handled using normal sterile procedures. In each instance, the cover sheet of the plate was turned back, and a 1 ml aliquot of a mold suspension was added to the center of the plate. After the sample reconstituted the medium (on the order of several seconds), the cover sheet was folded back to completely cover the medium. The plate was left to incubate for 5 days at 25° C., and then examined visually using a Quebec counter. The results are set forth in TABLE B below.

TABLE B

| | Colony Counts Plate Number | | | | |
|---|---|---|---|---|---|
| Mold Sample | 1 | 2 | 3 | 4 | 5 |
| Aspergillis niger | 400 | 400 | EG | NG | NG |
| Paecilomyces | 125 | 140 | EG | NG | NG |
| Aspergillis candida | 330 | 320 | EG-245 | NG | 320 |
| Fusarium trichincturn | 35 | 40 | 4 | NG | NG |
| Mold-unidentified | 135 | 120 | EG | EG | NG |

TABLE B indicates the number of colonies counted after 5 days incubation at 25° C. In some cases, colonies were not counted and only growth pattern was noted as follows:

NG—No growth of mold
EG—Edge growth. Mold colonies grew around the perimeter of the inoculated area. Taken as an indication of insufficient air supply to the center of the medium.

As seen in TABLE B, mold growth is improved in devices of the invention. Plates 1 and 2 have membranes with Gurley porosity values of about 0.1 and about 25, respectively. These plates show similar results, with colonies growing throughout the medium. Plates 3 and 4, with less porous membranes, generally show fewer colonies, edge growth, or no growth. Plate 5, with no membrane, generally shows no growth. Thus, it is seen that mold growth is generally dependent on the relative porosity of the membrane, with most improved growth seen when the membrane has a Gurley porosity value of about 25 or less. The results for *Aspergillis candida*, particularly the high level of growth on Plate 5 (without a membrane) are unexplained, but do not appear to be artifact.

We claim:

1. A device for growing microorganisms, which device comprises a body member, which body member comprises
   (1) a waterproof substrate having a top surface and a bottom surface;
   (2) an air-permeable membrane, having its peripheral edge(s) substantially uncovered, and having a top surface and a bottom surface, the bottom surface being fixed to and covering at least a portion of the top surface of the substrate; and
   (3) cold-water-reconstitutable dry medium fixed to and covering at least a portion of the top surface of the membrane so as to define a growth region and comprising at least one ingredient selected from the group consisting of one or more gelling agents and one or more nutrients for growing microorganisms.

2. A device according to claim 1, wherein the air-permeable membrane is a microporous film or non-woven web of synthetic or natural material.

3. A device according to claim 2, wherein the membrane is a material selected from the group consisting of polypropylene, polyethylene, polyethylene terephthalate, polybutylene terephthalate, nylon, polyvinylidine fluoride, rayon, and copolymers and blends thereof.

4. A device according to claim 1, wherein the membrane has a Gurley porosity value of less than about 100 seconds.

5. A device according to claim 1, wherein the membrane has a Gurley porosity value of less than about 50 seconds.

6. A device according to claim 1, wherein the membrane has a Gurley porosity value of less than about 25 seconds.

7. A device according to claim 1, wherein the membrane is between about 20 μm and about 100 μm thick.

8. A device according to claim 1, wherein the membrane is between about 40 μm and about 80 μm thick.

9. A device according to claim 1, further comprising cover means disposed adjacent to the dry medium and having a surface facing the dry medium, which cover means is substantially impermeable to microorganisms and water vapor and configured so as to cover at least the growth region.

10. A device according to claim 9, wherein the cover means is a cover sheet adhered in a hinge-like fashion along one edge of the body member.

11. A device according to claim 1, wherein the dry medium comprises a powder, and which device further comprises a layer of adhesive on at least said portion of the top surface of the membrane, the adhesive being insoluble in water and substantially non-inhibitory to the growth of the microorganisms, and wherein the powder is adhered substantially uniformly to the layer of adhesive.

12. A device according to claim 11, wherein the gelling agent is selected from the group consisting of locust bean gum, xanthan gum, and mixtures thereof.

13. A device according to claim 11, wherein the adhesive is a copolymer of 2-methylbutylacrylate and acrylic acid in a mole ratio of 90:10, respectively.

14. A device according to claim 11, wherein the layer of adhesive on the top surface of the membrane contains a dye that is metabolized by or otherwise reacts with microorganisms in order to cause the microorganisms to be colored or fluorescent.

15. A device according to claim 1, wherein the dry medium further comprises a bacteriostatic or bacteriocidal agent suitable to allow the growth of molds.

16. A device according to claim 9 additionally comprising a coating on the surface of the cover means facing the dry medium, which coating comprises (i) a layer of adhesive, which adhesive is insoluble in water and is substantially non-inhibitory to the growth of the microorganisms, and (ii) powder, which powder is cold-water-soluble and comprises at least one ingredient selected from the group consisting of one or more gelling agents and one or more nutrients for growing microorganisms, and which powder substantially uniformly adhered to the layer of adhesive on the cover sheet.

17. A device according to claim 1, wherein the dry medium comprises a coated medium.

18. A method of growing microorganisms comprising:
   (1) reconstituting the dry medium of the device according to claim 9 with an aqueous test sample containing microorganisms;
   (2) placing the cover means over the reconstituted medium; and
   (3) incubating the device at a suitable temperature and for a suitable time to allow the growth of microorganisms.

* * * * *

UNITED STATES PATENT AND TRADEMARK OFFICE
CERTIFICATE OF CORRECTION

PATENT NO. : 5,089,413
DATED : February 18, 1992
INVENTOR(S) : Robert L. Nelson et al.

It is certified that error appears in the above-identified patent and that said Letters Patent is hereby corrected as shown below:

Title page, item [75], "Paul E.L. Hansen" should read
--Paul E. Hansen--.

Col. 6, line 27, "cold-watersoluble" should read
--cold-water soluble--.

Signed and Sealed this

Twenty-first Day of September, 1993

Attest:

BRUCE LEHMAN

Attesting Officer       Commissioner of Patents and Trademarks